United States Patent [19]

Sauk et al.

[11] Patent Number: 4,780,450

[45] Date of Patent: Oct. 25, 1988

[54] PHYSICALLY STABLE COMPOSITION AND METHOD OF USE THEREOF FOR OSSEOUS REPAIR

[75] Inventors: John J. Sauk, Ellicott City, Md.; Craig L. Van Kampen, Oakdale, Minn.

[73] Assignees: The University of Maryland at Baltimore, Baltimore, Md.; Minnesota Mining and Manufacturing, St. Paul, Minn.

[21] Appl. No.: 78,598

[22] Filed: Jul. 28, 1987

Related U.S. Application Data

[63] Continuation-in-part of Ser. No. 811,677, Dec. 20, 1985, Pat. No. 4,698,326.

[51] Int. Cl.$^4$ ................... A61K 37/02; A61K 37/12
[52] U.S. Cl. ............................. 514/2; 514/7; 623/16
[58] Field of Search ................... 514/7, 2; 623/16

[56] References Cited

U.S. PATENT DOCUMENTS 4,563,350  1/1986  Nathan et al. ................ 424/98
4,619,655  10/1986 Hanker et al. ................ 623/16

FOREIGN PATENT DOCUMENTS 197693  10/1986  European Pat. Off. .

OTHER PUBLICATIONS

R. E. Grundel et al., 33rd Annual Meeting, Orthopaedic Res. Society, San Francisco, Calif. (Jan. 19–22, 1987).
M. Jarcho, *Clinical Orthopaedic and Related Research*, 157, 259 (1981).

*Primary Examiner*—Sam Rosen
*Attorney, Agent, or Firm*—Merchant, Gould, Smith, Edell, Welter & Schmidt

[57] ABSTRACT

A composition for osseous repair which is prepared by a process comprising mixing a particulate polycrystalline calcium phosphate ceramic, a phosphophoryn calcium salt and type I collagen, preferably in a weight ratio of ceramic:calcium salt:collagen of about 775-15-:3-0.1:1, to yield a solid porous composition which is effective to promote new bone formation upon introduction of the composition into osseous defects.

11 Claims, No Drawings

PHYSICALLY STABLE COMPOSITION AND METHOD OF USE THEREOF FOR OSSEOUS REPAIR

CROSS-REFERENCE TO RELATED APPLICATION

This application is a continuation-in-part of U.S. application Ser. No. 811,677, filed Dec. 20, 1985, now U.S. Pat. No. 4,698,326.

BACKGROUND OF THE INVENTION

Currently, the most effective method for treatment of severe or nonhealing osseous defects is autogenic bone grafting, which involves the transplantation of bone from another part of a patient's body into the defect. Significatn disadvantages are associated with autogenic bone grafting, including donor site morbidity and limited tissue availability. Bone banks have been established to provide an alternative source of bone grafting material, consisting of allogenic freeze-dried bone. Allogenic bone grafts, however, are very expensive and do not heal as well as do fresh autogenic bone grafts.

Attempts to overcome these problems have involved the use of calcium phosphates and apatites. They have been evaluated as either dense or porous implants, with various types and sizes of porosity, including replicas of marine coral. Hydroxylapatite implants are generally considered to be somewhat more stable in vivo than tricalcium phosphate implants, which show a greater tendency to be absorbed. These ceramic materials are generally implanted in particulate form to fill bone defects, which can present handling difficulties.

Hydroxylapatite and tricalcium phosphate particles both apparently provide a useful scaffold for bone ingrowth into a bone defect, but these ceramics do not have any inductive or accelerating effect on bone repair. A significant problem with implants of calcium phosphate mineral particles relates to keeping the particles at the implantation site. Various approaches have been used to try to inhibit migration of the mineral particles from the implanation site, including adding the particles to a collagen matrix and mixing the particles with plaster of paris (See European patent application No. 197,693, and U.S. Pat. No. 4,619,655, respectively).

Demineralized, lyophilized bone has also been used as a component of osteoinductive agents. See M. R. Urist, *Science*, 150, 893 (1965). Recently, M. R. Urist et al., in U.S. Pat. No. 4,294,753 and in *Proc. Natl. Acad. Sci. U.S.A.*, 76, 1828 (1979), have disclosed the use of particles such as "protein osteoinductive factor" (OF) derived from such bone matrices with various carriers to induce new bone formation. However, it can be difficult to reproducibly prepare these materials, which must be characterized by various bioassay systems. See, for example, R. Nathan et al., U.S. Pat. No. 4,563,350.

Sauk and Van Kampen disclose compositions which are effective to promote new bone formation upon introduction of the composition into osseous defects in U.S. Pat. application Ser. No. 811,677, filed Dec. 20, 1985, now U.S. Pat. No. 4,698,326, the disclosure of which is incorporated by reference herein. Preferred compositions are prepared by mixing a phosphophoryn calcium salt and type I collagen in a ratio of the salt to the collagen of about 3.0–0.1:1 to yield a solid composition. These compositions have the appearance and texture of soft sponges. The low mechanical strength and highly compressible nature of these sponges can limit their application in the treatment of segmental defects.

Therefore, a need exists for physically stable compositions useful to repair osseous defects which can be readily manipulated during formulation and implantation. A further need exists for compositions useful for osseous repair which can be prepared reproducibly, e.g., which incorporate well characterized components.

BRIEF DESCRIPTION OF THE INVENTION

The present invention is directed to a solid composition which is prepared by a process comprising mixing a phosphophoryn calcium salt and type I collagen in a salt:collagen weight ratio of about 3.0–0.1:1, preferably about 2.5–0.5:1, with a large about of a particulate polycrystalline calcium phosphate ceramic to yield a solid matrix. The particulate ceramic is employed in an amount which is effective to substantially improve the physical stability of the matrix of the resultant porous solid. The resultant spongy solid is resilient but is substantially less compressible than the sponges disclosed in Ser. No. 811,677. Therefore, it is easier to predetermine the amount of the present composition which will suffice to completely fill a given defect void. Furthermore, the present compositions are more rigid, and thus, provide more tactile feedback to the surgeon or dentist performing the implant. Thus, they can be more easily applied to and positioned in the defect.

The present invention is also directed to the use of these compositions to promote bone formation upon their introduction into osseous defects. It is believed that the particulate calcium phosphate ceramics will enhance the long-term repair and remodeling of new bone in osseous defects over that obtainable with implant compositions consisting essentially of phosphophoryn calcium or phosphophoryn calcium-collagen.

Therefore, the compositions of the present invention are useful as bone graft substitutes in the repair of osseous defects and to promote osseous formation. For example, they are useful to fill defects created during the treatment of osteosarcomas or bone cysts, to promote the repair of nonunions and to repair alveolar clefts. The present compositions are at least partially absorbed in a short period after initiating a cascade of events which leads to their complete replacement of new bone. The compositions of the present invention are particularly useful for the treatment of large osseous defects, where there is a requirement for a rapid diminishment of an osseous void in order to re-establish the cortical plate and reduce the possibility of fracture. Furthermore, the present compositions are well-characterized and can be obtained reproducibly.

DETAILED DESCRIPTION OF THE INVENTION

According to the present invention, new bone formation can be promoted in vivo in osseous defects by introduction thereinto of a composition comprising phosphophoryn calcium. To facilitate manipulation by the physician and to provide a structure to direct the desposition of new bone, these compositions preferably comprise a mixture of phosphophoryn calcium, a matrix material such as type I collagen and a particulate calcium phosphate ceramic. These compositions are intended to facilitate matrix-mediated mineralization, whereby the collagen defines a structural matrix and the phosphophoryn salt regulates and directs mineral deposition in terms of its location, crystallinity and association with the calcium phosphate ceramic particles. The calcium phosphate particles also interact with the collagen to improve the physical properties of the collagen matrix by reducing its compressibility and increasing its mechanical strength.

Thus, the present compositions do not simply provide a static physical "scaffold" for bone ingrowth, but are believed to create a dynamic ionic front that accelerates new bone formation by mimicking the mineralization front created by dentin in vivio. Another advantage of the invention is that the compositions are able to be partially absorbed after initiating a cascade of events that leads to a more rapid and complete replacement of osseous voids than can be accounted for by normal wound healing processes.

Phosphophoryn Salt

Phosphophoryns are acidic, phosphorous-containing proteins which can be isolated from the noncollagenous proteins which are constituents of the organic extracellular matrix of certain mineralized tissues. In vivo, these proteins may act to initiate the calcification of dentin by chelating calcium ions. Purified dentinal phosphophoryn has a high affinity for calcium ion ($Ca^{+2}$). Its binding sites exhibit dissociation constants (Kd) of $1.3 \times 10^{-7}$M and $0.85 \times 10^{-5}$M. However, sodium, potassium and magnesium ions can effectively compete with $Ca^{+2}$ for these binding sites. The calcium salts of phosphophoryn employed in the present invention may reduce this deleterious competitive binding.

Conventional methods for the purification of the preferred dentinal phosphophoryn employ precipitation of decalcified dentin with calcium salts. Following purification, these salts can be employed as the dentinal phosphophoryn calcium component in the present compositions. The purification of dentinal phosphophoryn has been described by W. T. Butler et al., *Collagen Rel. Res.*, 1, 187 (1981) and by D. Cocking-Johnson et al., in *Collagen Rel. Res.*, 3, 505 (1983), the disclosures of which are incorporated by reference herein.

Synthetic phosphophoryns may be produced in the laboratory by recombinant DNA techniques. Alternatively, phosphophoryn analogs useful in the present invention may be chemically synthesized by conventional reactions employed in polypeptide synthesis.

Collagen

Collagen is the general designation of a group of at least four connective tissues proteins which are designated as types I-IV. Type I collagen accounts for a large part of the organic mass of bone, and has also been isolated from intervertebral disc, liver, tendon and kidney tissue, and in combination with type III collagen from skin, sclera and spleen. The precipitational behavior of native pepsin-resistant collagen molecules at relatively low ionic strength has been used extensively for their purification from other proteins. In addition, differential solubilities have been observed for types I, II and III collagens which can be fractionated from one another by precipitation at different salt concentrations at neutral pH. For example, at acidic pHs, both type I collagen and type III collagen derived from skin precipitate at 0.7-0.9M NaCl concentration, while at neutral pH, type I precipitates at 2.6M NaCl while type III precipitates in 1.5-1.7M NaCl. See E. H. Epstein, Jr., *J. Biol. Chem.*, 249, 3225 (1974).

Due to the difficulties encountered in preparing pure collagen of a given type, the term "type I collagen" as used herein is intended to refer to pure type I collagen and any collagen preparation which comprises a substantial proportion of type I collagen, preferably at least a major proportion of type I collagen.

Calcium Phosphate Ceramic

Polycrystalline calcium phosphate ceramics useful in the present compositions are generally formed by the high temperature sintering of various calcium phosphate minerals. These minerals are found commonly in nature and also can be prepared synthetically by well-known solution precipitation techniques. A particular calcium phospahte, namely tribasic calcium phosphate (hydroxylapatite), is the mineral component of bones and teeth. Therefore, calcium phosphate-based ceramics have been evaluated as hard tissue implants. The most widely investigated polycrystalline calcium phosphate ceramic implants employ tribasic calcium phosphate (hydroxylapatite, [$Ca_{10}(PO_4)_6(OH)_2$]), or beta-tricalcium phosphate [$Ca_3(PO_4)_2$]. The preparation and properties of these and other useful ceramic materials is discussed in a review article by M. Jarcho, in *Clinical Orthopaedics and Related Research*, 157, 259 (1981), the disclosure of which is incorporated by reference herein.

The choice of any given particulate calcium phosphate ceramic will be directed by (a) the particle size, (b) the particle density, (c) the desired matrix density, and (d) the desirability of particle absorption. For example, the preferred polycrystalline calcium phosphate ceramics for use in the present compositions consist of small particles of dense hydroxylapatite (ca. 1-10 microns in diameter), which are readily supported by relatively low density (ca. 0.5-1.5 mg/cc) phosphophoryn calcium-collagen matrices. Larger particles of dense hydroxylapatite of a size greater than about 100 microns in diameter can be supported by a more dense (ca. 2.5-7.5 mg/cc) phosphophoryn calcium-collagen matrix. Because of the specific gravity of dense tricalcium phosphate is approximately the same as that of hydroxylapatite, it follows that tricalcium phosphate particles of similar size can be substituted for hydroxylapatite. Mixtures of these two materials can also be used. It may be possible to use large-sized particles of porous calcium phosphate minerals in the lower density phosphophoryn calcium-collagen matrix because the lower density of the porous particles should allow larger particles to be supported by the matrix.

Preparation

The compositions of the present invention can be prepared by adding the desired amount of the phosphophoryn calcium salt as a powder to an aqueous solution containing the desire amount of collagen. The powdered calcium phosphate ceramic is then added, and the water is removed in vacuo, e.g., by lyophilization. The resultant material is a tan, hardened sponge which can be directly implanted into osseous defects without further purification.

The preferred compositions are prepared by mixing the particulate calcium phosphate ceramic, phosphophoryn calcium, and type I collagen in a wieght ratio of about 775-15:3-0.1:1, preferably about 400-20:3-0.1:1, most preferably about 200-35:2.5-0.5:1. One particularly preferred embodiment employs a weight ratio of hydroxylapatite:dentinal phosphophoryn calcium:type I collagen of about 90:1:1.

The invention will be further described by reference to the following detailed examples.

EXAMPLE I

A PHYSICALLY STABLE OSSEOUS REPAIR COMPOSITIONS

1. Materials

A. Dentinal Phosphoryn Calcium Salts

Small pieces of cleaned bovine dentin were stirred for 18 hr at 4° C. in 4M guanidine-HCl containing four protease inhibitors [1 mM iodoacetate, 1 mM phenylmethylsulfonyl fluoride (PMSF), 1 mg/ml soybean trypsin inhibitor and 5 mM n-ethylmaleimide]. The dentin was rinsed thoroughly with water, placed in dialysis bags and decalcified by dialyssi against 0.25M EDTA containing the protease inhibitors at 4° C. Decalcification required a minimum of 3 changes of EDTA, each exposure lasting at least 72 hours. The supernatant inside the dialysis bags was isolated and dialyzed against distilled water for at least 4 days. The phosphophoryns were then precipitated with calcium chloride as described by Y. Kuboki et al., *J. Dent. Res.*, 58, 1926 (1979) and the mixture was stirred for 18 hr at 25° C. The dentinal phosphophoryn calcium slats were isolated by centrifugation, washed with 1.0M aqueous CaCl₂ and dried by lyophilization.

B. Unenriched Bovine Skin Collagen

Bovine skin was digested with 1 mg/ml pepsin and the crude product precipitated with NaCl (0.7M). The collagen was then dialyzed extensively against 0.5M acetic acid and lyophilized. The supernatant was treated with NaCl (1.5M) to yield a precipitate which was dialyzed extensively against 0.5M acetic acid and lyophilized to yield the product.

C. Type I and Type III Collagen

Collagen was prepared from bovine skin by the procedure of Uitto as described in *Arch. Biochem. and Biophys.*, 371–379 (1979). Accordingly, samples of calf skin were dissected and the subcutaneous tissues removed. The specimens were then rinsed with cold (+4° C.) 0.15M NaCl—0.05M Tris—HCl, pH 7.5. The skin was then minced extensively with scissors in 0.5M acetic acid. Pepsin (Worthington Diagnostics, Freehold, NJ, 2X crystallized) was added to a final concentration of 0.1 mg/ml, and the samples were incubated at 4° C. for 16 hr. At the end of the incubation period, the homogenate was centrifuged at 30,000 g for 60 min at 4° C. The pellet was then dissolved and adjusted to pH 8.5 with cold 1.0M NaOH, and extensively dialyzed against 0.4M NaCl—0.1M Tris—HCl, pH 7.5.

In order to separate type I collagen, the solubilized material was fractionated by the sequential precipitations with 1.5 and 2.5M NaCl. After the slow addition of solid NaCl to any given concentration, the samples were stirred for 24 hr at 4° C. and then centrifuged at 30,000 g for 60 minutes.

The pellet resulting from precipitation at 2.5M NaCl was dissolved in and dialyzed against 0.5M acetic acid and then lyophilized. The type I-enriched collagen appears as a soft white spongy substance.

The pellet resulting from the precipitation with 1.5M NaCl at neutral pH consists of a 1:1 distribution of type I and type III collagen. See J. Uttio, *Arch. Biochem. Biophys.*, 192, 371 (1979).

D. Osseous Repair Compositions

Bovine type I collagen was dissolved in 0.5M acetic acid at 4° C. for 24 hr with constant mixing. The resulting solutions were then centrifuged at 30,000 g for 30 min and the supernatant collected. The concentration of the collagen was adjusted to 1 mg/ml by measuring the absorption at 247nm for which a standard curve has been created based on absorption and hydroxyproline ratios. To these latter collagen solutions, 1 mg/ml of phosphophoryn calcium was added followed by particulate hydroxylapatite in the vol. (phosphophoryn calcium-collagen solution):vol. (mineral) ratios summarized on Table 1, below.

TABLE 1

| Example | Volume Phosphophoryn $Ca^{+2}$-Collagen Mixture* | Volume Hydroxylapatite Powder** |
|---------|---|---|
| A | 1 | 1.0 |
| B | 1 | 0.5 |
| C | 1 | 0.25 |
| D | 1 | 0.1 |

*1 mg/ml phosphophoryn-$Ca^{+2}$ and 1 mg/ml type I collagen in 0.5 M acetic acid.
**1–10 micron diameter particles (361 mg/cc)

The range of hydroxylapatite mineral to aqueous phosphophoryn-collagen mixture that possessed the most desired qualities was 0.5–0.1:1 (vol:vol.) This represents a weight ratio of mineral:phosphophoryn calcium:collagen of 180–35:1:1. The most preferred quality of materials was achieved at a ratio of calcium phosphate mineral to aqueous phosphophoryn-collagen mixture of 1:0.25 vol:vol. This is a weight ratio of mineral:phosphophoryn calcium:collagen of 90:1:1.

All of the compositions prepared with a starting collagen solution concentration of 1 mg/cc and with fine hydroxylapatite mineral particles of about 1–10 microns in size possessed the hardened, sponge-like characteristics desired for an osseous replacement matrix. Samples prepared with larger particles of hydroxylapatite mineral (759 mg/cc) required a starting collagen solution concentration of 5 mg/cc to support the mineral particles in the matrix.

The invention has been described with reference to various specific and preferred embodiments and techniques. However, it should be understood that many variations and modifications may be made while remaining within the spirit and scope of the invention.

What is claimed is:

1. A composition for osseous repair which is prepared by a process comprising mixing a particulate polycrystalline calcium phosphate ceramic, a phosphophoryn calcium salt and type I collagen in a weight ratio of ceramic:calcium salt:collagen of about 775–15:3–0.1:1 to yield a solid porous composition which is effective to promote new bone formation upon introduction of the composition into osseous defects.

2. The composition of claim 1 wherein a mixture of the particulate ceramic, the phosphophoryn calcium salt and the type I collagen in water is prepared and the water is removed in vacuo.

3. The composition of claim 2 wherein the water is removed by lyophilization.

4. The composition of claim 1 wherein the particulate polycrystalline calcium phosphate ceramic comprises hydroxylapatite, beta-tricalcium phosphate or mixtures thereof.

5. The composition of claim 1 which comprises a dentinal phosphophoryn calcium salt.

6. The composition of claim 1 wherein the weight ratio of ceramic:calcium salt:collagen is about 400–20-:3–0.1:1.

7. A composition for osseous repair which is prepared by a process comprising mixing particulate hydroxylapatite, a phosphophoryn calcium salt and type I collagen in a weight ratio of hydroxylapatite:phosphophoryn calcium salt:collagen of about 200-35:2.5-0.5:1, to yield a solid porous composition which is effective to promote new bone formation upon introduction of the composition into osseous defects.

8. The composition of claim 7 wherein the hydroxylapatite particles are about 1-10 microns in diameter.

9. The composition of claim 7 wherein the weight ratio of phosphophoryn calcium salt to collagen is about 1:1.

10. A method for the repair of an osseous defect comprising introducing into said defect an amount of the composition of claim 1 effective to promote new bone formation.

11. A method for the repair of an osseous defect comprising introducing into said defect an amount of the composition of claim 7 effective to promote new bone formation.

* * * * *

UNITED STATES PATENT AND TRADEMARK OFFICE
CERTIFICATE OF CORRECTION

PATENT NO. : 4,780,450

DATED : October 25, 1988

INVENTOR(S) : John J. Sauk and Craig L. Van Kampen

It is certified that error appears in the above-identified patent and that said Letters Patent is hereby corrected as shown below:

At Col. 1, lines 51-52, for "the use of particles such as" read --the use of proteins such as--.

At Col. 2, line 15, for "with a large about of" read --with a large amount of--.

At Col. 2, line 45, for "replacement of new bone" read --replacement by new bone--.

At Col. 2, line 61, for "desposition of new" read --deposition of new--.

At Col. 3, line 49, for "tissues proteins" read --tissue proteins--.

At Col. 4, line 13, for "calcium phospahte" read --calcium phosphate--.

At Col. 4, line 38, for "Because of the specific" read --Because the specific--.

UNITED STATES PATENT AND TRADEMARK OFFICE
CERTIFICATE OF CORRECTION

PATENT NO. : 4,780,450

DATED : October 25, 1988

INVENTOR(S) : John J. Sauk and Craig L. Van Kampen

It is certified that error appears in the above-identified patent and that said Letters Patent is hereby corrected as shown below:

At Col. 4, line 61, for "in a wieght ratio" read --in a weight ratio--.

At Col. 5, line 14, at "by dialyssi against" read --by dialysis against--.

Signed and Sealed this

Twenty-fifth Day of July, 1989

Attest:

DONALD J. QUIGG

Attesting Officer

Commissioner of Patents and Trademarks